(12) United States Patent
Serhan et al.

(10) Patent No.: US 8,425,543 B2
(45) Date of Patent: Apr. 23, 2013

(54) ANNULAR NUCLEUS PULPOSUS REPLACEMENT

(75) Inventors: Hassan A. Serhan, S. Easton, MA (US); Andrew Dooris, Fall River, MA (US)

(73) Assignee: DePuy Acromed, Raynham, MA (US)

( * ) Notice: Subject to any disclaimer, the term of this patent is extended or adjusted under 35 U.S.C. 154(b) by 459 days.

(21) Appl. No.: 11/300,056

(22) Filed: Dec. 14, 2005

(65) Prior Publication Data

US 2006/0106410 A1    May 18, 2006

Related U.S. Application Data

(62) Division of application No. 10/334,598, filed on Dec. 31, 2002, now Pat. No. 7,004,971.

(51) Int. Cl.
 *A61B 17/22*    (2006.01)
(52) U.S. Cl.
 USPC .............. 606/159; 606/80; 606/180; 606/246

(58) Field of Classification Search ............... 128/898; 604/22; 606/79, 80
See application file for complete search history.

(56) References Cited

U.S. PATENT DOCUMENTS

| | | | |
|---|---|---|---|
| 5,702,449 A | 12/1997 | McKay | |
| 5,865,845 A | 2/1999 | Thalgott | |
| 5,890,268 A | 4/1999 | Mullen et al. | |
| 5,981,826 A | 11/1999 | Ku et al. | |
| 6,127,597 A * | 10/2000 | Beyar et al. | 606/86 |
| 6,264,695 B1 | 7/2001 | Stoy | |
| 6,712,853 B2 | 3/2004 | Kuslich | |
| 2001/0031981 A1* | 10/2001 | Evans et al. | 606/200 |
| 2002/0026244 A1 | 2/2002 | Trieu et al. | |
| 2002/0147497 A1 | 10/2002 | Belef et al. | |
| 2003/0191474 A1* | 10/2003 | Cragg et al. | 606/79 |
| 2003/0199979 A1 | 10/2003 | McGuckin, Jr. | |
| 2005/0055099 A1 | 3/2005 | Ku | |

* cited by examiner

*Primary Examiner* — Thomas J Sweet
*Assistant Examiner* — Christopher D Prone

(57) ABSTRACT

A method of removing a nucleus pulposus from an intervertebral disc, involving rotating a distal end head of an instrument so that flexible protrusions thereon will cut nucleus pulposus native material.

3 Claims, 6 Drawing Sheets

ANNULAR NUCLEUS PULPOSUS REPLACEMENT

CONTINUING DATA

Figure 1:
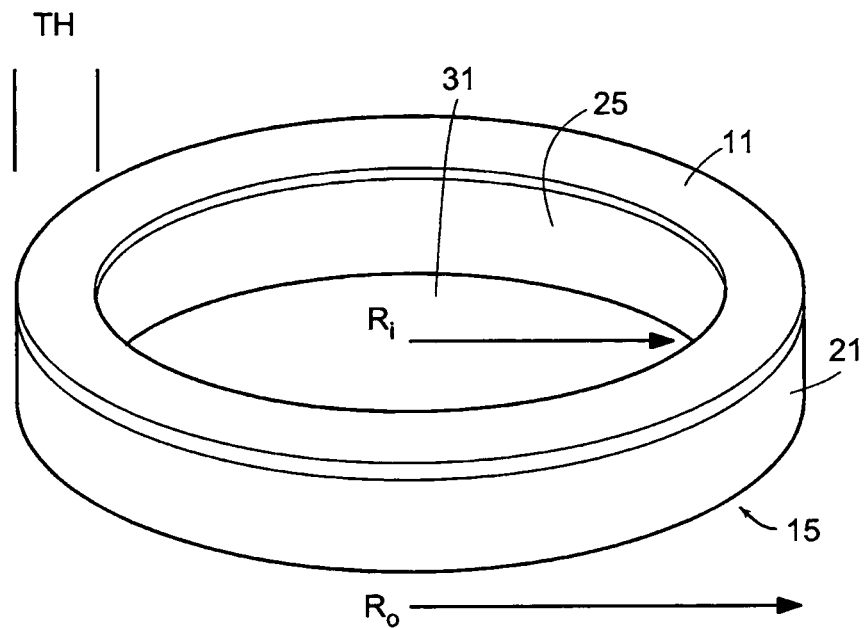

This divisional patent application claims priority from U.S. Ser. No. 10/334,598, filed Dec. 31, 2002, entitled "Annular Nucleus Pulposus Replacement" (Serhan), now U.S. Pat. No. 7,004,971.

BACKGROUND OF THE INVENTION

Intervertebral disc degeneration causes a number of clinical problems relating to reduced disc height and herniation. In many cases, a simple discectomy can effectively relieve pain, but in time results in further collapse of the disc space because the intervertebral disc can no longer resist body loads the same as a healthy disc. Spine fusion procedures represent another state of the art treatment for disc problems. Fusion generally involves the use of interbody fusion cages and spinal fixation systems to immobilize the fusion site. However, it would be desirable to provide pain relief to the patient without substantially reducing the patient's range of motion.

In an effort to substantially maintain the patient's range of motion, the art has considered nucleus pulposus replacement and enhancement devices. Many of these devices are designed to fill at least a portion of the void left by removal of the nucleus pulposus portion of the disc and provide joint flexibility and shock absorption. Some of the nucleus pulposus devices being evaluated are in situ cured (such as in situ cured polyurethane contained within an outer bladder and in situ cured protein polymers). However, the fluid nature of these in situ cured materials provides the potential for these materials seep out of the disc space both intraoperatively and postoperatively. Other devices under evaluation include relatively solid hydrogels (such as hydrogel contained within a UHMWPE pillow and hydrogel balls). However, these hydrogel devices suffer from problems related to migration out of the disc space (expulsion) and subsidence.

US Published Patent Application No. 2002/0147497 ("Belef") discloses a substantially flexible elongate body of fill material 412 which may be introduced through an opening in the annulus fibrosis. The body of fill material is fed through the opening until it substantially fills the interior of the disc. See FIG. 7 of Belef.

US Published Patent Application Number US 2002/0026244 ("Trieu") discloses a first nucleus pulposus replacement device having a load-bearing elastic body surrounded by a deformable outer shell.

In a second embodiment, such as FIGS. 15 and 16, Trieu discloses a shape memory implant configured to form a spiral or other annular shape. These implants are deformable from a first folded state to a second substantially straight shape. In the first state, the device can be inserted into a disc space through a minimal access tube, and in a second state, the device can take on an annular shape in order to conform to the inner wall of the annulus fibrosus.

Although the devices of Trieu provide desirable load-bearing and minimal access qualities, they appear to transfer load through the center of the natural endplates. For example, in the first embodiment of Trieu, the middle of the device is completely filled with the inner elastic body. In the second embodiment, the inner hole is so small that the middle portion of the body is still substantially filled with the shape memory material. Because the middle portion of the natural endplates are typically weaker than the peripheral portions, transferring load to the central portion of the endplates may be mechanically problematic by causing adverse stress shielding of the annulus and possible endplate fracture.

In addition, the devices of Trieu may also be susceptible to slippage. For example, in the first embodiment of Trieu, the outer shell envelops the inner elastic body in all directions. If the outer shell moves laterally, there is nothing to prevent further lateral movement. In the second embodiment, the inner hole is fairly small and so any tissue growing therethrough may not stabilize the device.

In addition, because the disc changes shape during natural spinal movement, the Trieu devices will also deform. Lastly, because the ends of the spiral Trieu devices overlap, the Trieu device produces internal sliding interfaces. Natural spinal movement may produce wear debris at these internal sliding interfaces.

SUMMARY OF THE INVENTION

In a first aspect of the present invention, the present inventors have developed an annular nucleus pulposus replacement device having a large central recess. Since the load bearing portions of this device are substantially located on its periphery, the device transfers load to the periphery of the endplates while leaving the central region generally unloaded.

In some embodiments, the recess is a large central throughhole. This throughhole provides an opportunity for a large column of tissue to grow therethrough and connect the opposing endplates. This large column of tissue should substantially prevent any further slippage of the device. The device may also serve to retain the bone in the central portion of the disc space.

In some preferred embodiments, the present invention has two states. The first state allows the device of the present invention to be inserted into the disc space after nucleotomy or discectomy without substantial disruption to the patient's physiology while the second states provides maintenance of the spinal segment range of motion and normal loading patterns on the vertebral endplates. Preferably, the first state is a folded state, and the second state is an unfolded state.

In some cases, immediate restoration of disc height with complete removal of pro-inflammatory tissues can be achieved using the preferred nucleus pulposus replacement devices of the present invention.

This invention is advantageous over the prior art for many reasons. Second, the throughhole embodiments offer a greater likelihood of maintaining the device's position within the disc space over the course of time because a stabilizing column of tissue can grow through the throughhole. First, the presence of the large recess distributes load away from the center of the vertebral endplate and towards the endplate periphery. This is desirable because the bone located in the endplate periphery is stronger than the bone located in the center of the endplate.

Therefore, in accordance with the present invention, there is provided a prosthetic nucleus pulposus replacement device comprising:

a) an outer surface having a radius and adapted to conform to an inner wall of an annulus fibrosus, and
b) an inner surface having a radius and defining a central recess, wherein the outer and inner surfaces define a load-bearing thickness therebetween, and
wherein the ratio of the radius of the inner surface to the radius of the outer surface is at least 30%.

Also in accordance with the present invention, there is provided a prosthetic nucleus pulposus replacement device comprising:

a) an upper surface adapted to bear against an upper endplate,
b) a lower surface adapted to bear against a lower endplate,
c) an outer surface having a radius and adapted to conform to an inner wall of an annulus fibrosus,
d) a through hole having a radius and extending from the upper surface to the lower surface,
wherein the ratio of the radius of the throughole to the radius of the outer surface is at least 30%.

Preferably, the ratio of the radius of the inner surface to the radius of the outer surface is at least 50%, more preferably at least 60%, more preferably at least 80%.

In embodiments, wherein the recess forms a throughhole, the throughhole preferably comprises at least 30 volume percent (vol %) of the device, more preferably at least 50%, and more preferably at least 75%. More preferably, the throughhole preferably comprises between 75 vol % and 90% vol of the device. Above 90 vol %, the lack of material may lead to undesirably high stress concentrations.

DETAILED DESCRIPTION OF THE FIGURES

FIG. 1 discloses a perspective view of an annular embodiment of the device of the present invention in its unloaded state.

Figure 2:
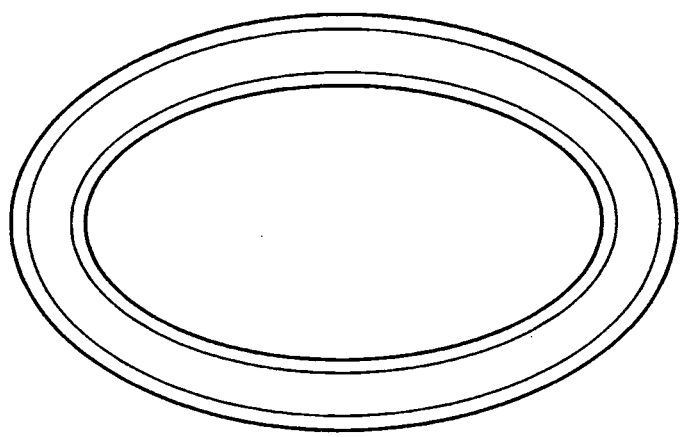

FIG. 2 discloses a top view of FIG. 1.

Figure 3:
Figure 4A:
Figure 4B:
Figure 4C:
Figure 4D:
Figure 4E:
Figure 4F:
Figure 4G:
Figure 4H:
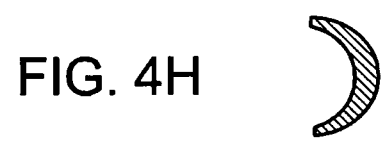
Figure 4I:

FIG. 3 discloses a top view of an annular embodiment of the device of the present invention in a folded state.

FIGS. 4a-4i disclose various cross sections of the thickness of the device of the present invention.

Figure 5A:
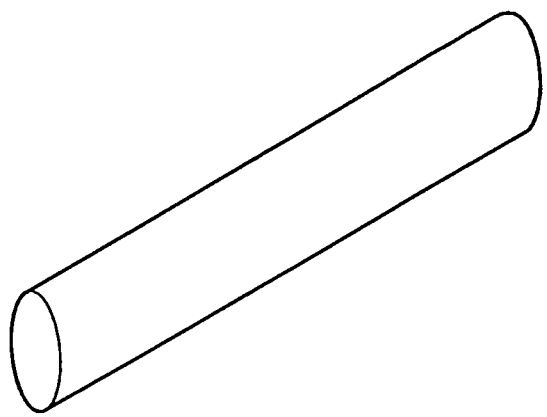
Figure 5B:
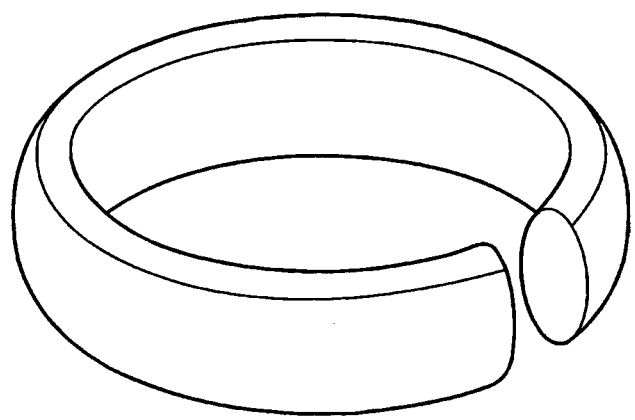

FIGS. 5a and 5b disclose respective perspective views of a split ring embodiment of the device of the present invention in its respective elongated and conforming states.

Figure 6:
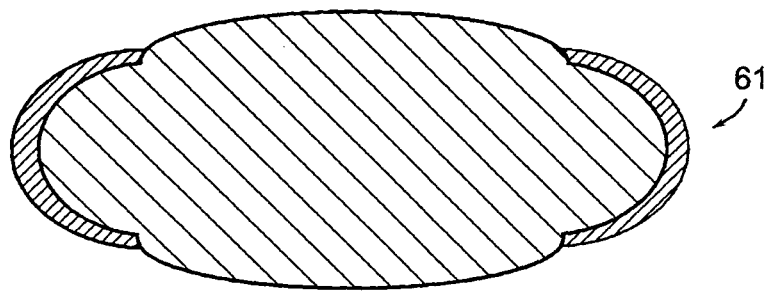

FIG. 6 discloses a cross section of the thickness of a device of the present invention, wherein the outer and inner surfaces thereof comprise a shape memory metal.

Figure 7:
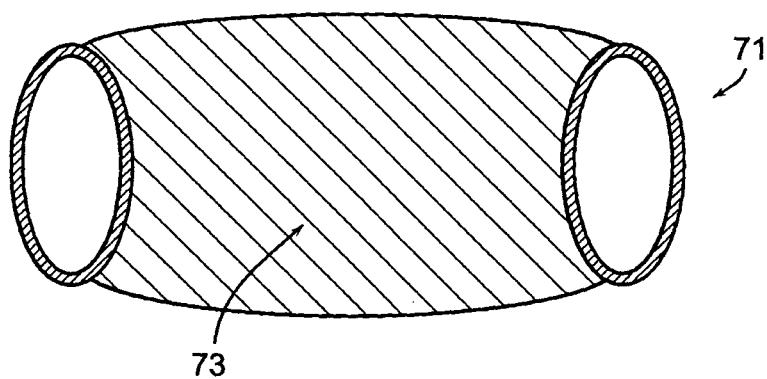

FIG. 7 discloses a side view of an annular embodiment of the device of the present invention, wherein the inner and outer surfaces comprises shape memory metal loops.

Figure 8:
Figure 9:
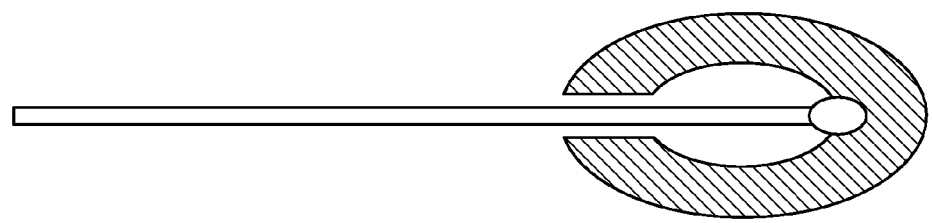

FIGS. 8 and 9 disclose respective cross-section and side views of a device of the present invention attached to an insertion instrument.

Figure 10:
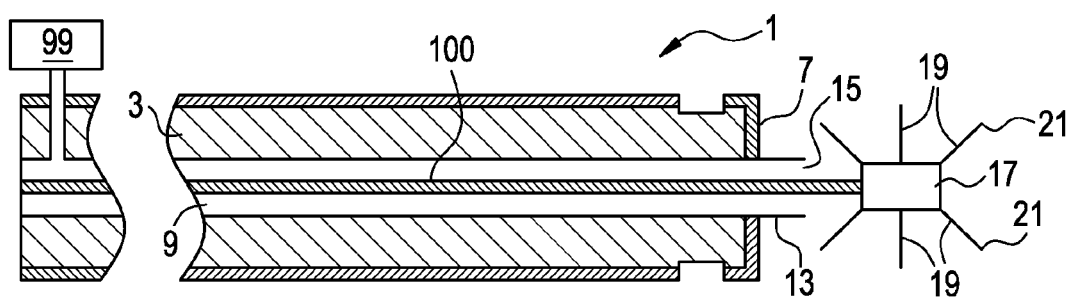
Figure 11:
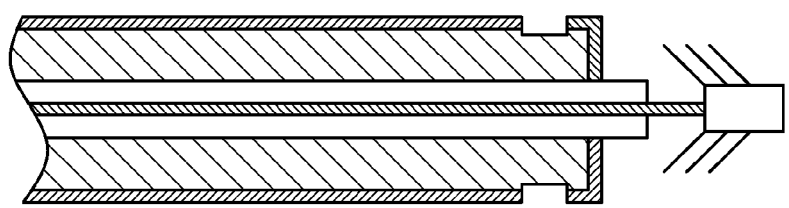
Figure 12:
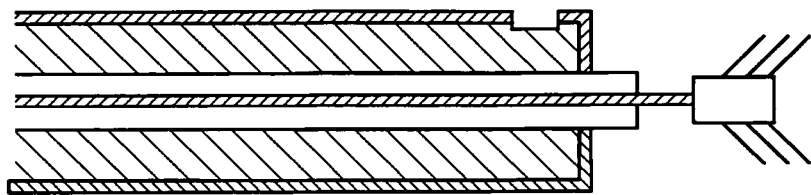

FIGS. 10-12 disclose cross-sections of an instrument adapted to remove the nucleus pulposus.

Figure 13:
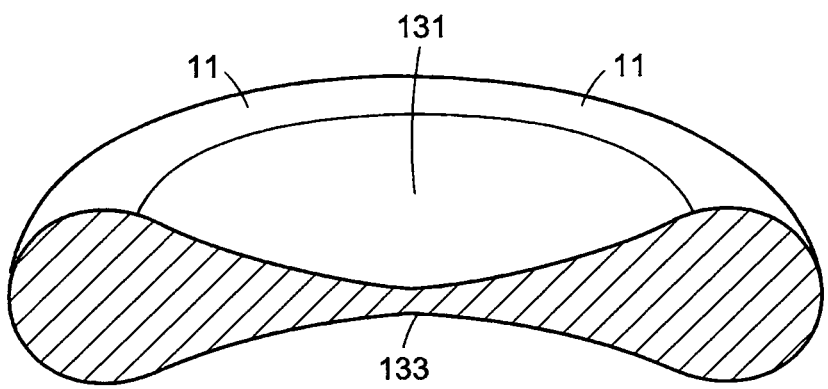

FIG. 13 discloses a perspective vertical cross-section of a device of the present invention comprising two closed recesses.

Figure 14:
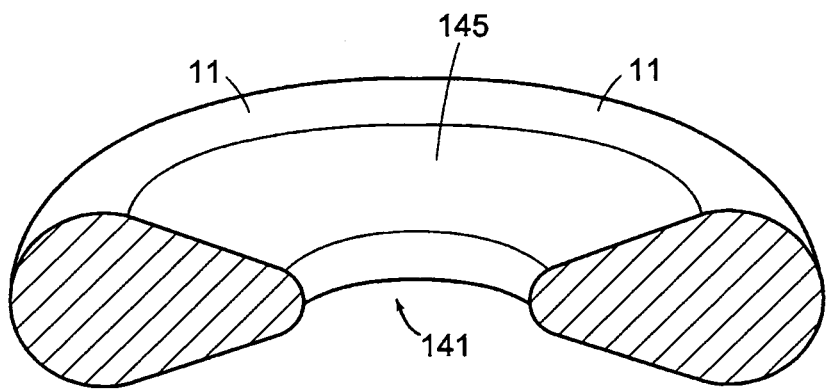

FIG. 14 discloses a perspective vertical cross-section of a device of the present invention having a transition zone.

DETAILED DESCRIPTION OF THE INVENTION

For the purposes of the present invention, a "compressible" material compresses under an axial load, and a "resilient" material regains its original shape when unloaded.

Now referring to FIG. 1, there is provided an annular prosthetic nucleus pulposus replacement device 1 comprising:
a) an upper surface 11 adapted to bear against an upper endplate,
b) a lower surface 15 adapted to bear against a lower endplate,
c) an outer surface 21 adapted to conform to an inner wall of an annulus fibrosus,
d) an inner surface 25 defining a thickness TH between the outer and inner surfaces, and
e) a recess 31 extending from the upper surface to the lower surface to form a through hole.

The function of the upper and lower surfaces is to bear against the upper and lower endplates, thereby maintaining the height of the natural disc space therebetween. Typically, the height between the bearing surfaces is between 4 mm and 12 mm. In some embodiments, these bearing surfaces are parallel. In other embodiments designed for use in the cervical spine, these surfaces form an angle of between 1 and 10 degrees, more preferably between 4 and 8 degrees. In other embodiments designed for use in the lumbar spine, these surfaces form an angle of between 1 and 25 degrees, more preferably between 8 and 12 degrees. In some cases having angled bearing surfaces, the height of the device is greater on the anterior side of the device, thereby providing lordosis. In other cases, the height of the device is greater on the posterior side of the device, thereby providing kyphosis. These bearing surfaces also define the inner and outer radii of the device.

The function of the outer surface of the device is to substantially conform to the inner wall of the natural annulus fibrosus.

In some embodiments in which the annulus is made of a flexible material, the outer surface of the device will move outward during axial compression and press against and adhere to the inner surface of the natural annular wall. This outward movement is desirable not only because it mimics the natural movement of the natural nucleus pulposus during compression, but also because it puts the annulus fibrosus in tension. If disc degeneration resulted in the annulus fibrosus becoming delaminated, then placing the annulus fibrosus in tension may be especially desirable because the tension will tend to bring together the individual layers of the laminated annulus which had been separated.

Since the inner wall of the annulus fibrosus has a rounded concave contour, the outer surface of the device, and particularly the anterior portion of the outer surface of the device, preferably has a complimentary rounded convex contour in a horizontal cross section. In some embodiments, the posterior portion of the outer surface of the device has a flat or concave horizontal cross section.

In some embodiments, the middle portion of the outer surface of the device extends further radially than the upper and lower portions of the outer surface to compliment the concave vertical cross section of the inner wall of the annulus fibrosus.

In some embodiments, the outer surface of the device conforms to at least a portion of the inner wall of the annulus fibrosus. In some embodiments, the outer surface of the device conforms to at least 50% of the circumference of the inner wall of the annulus fibrosus, preferably at least 75%, more preferably at least 90%.

In some embodiments, the outer surface of the device comprises a plurality of protrusions extending radially outward. These protrusions grab the inner wall of the annulus fibrosus and prevent rotation and migration.

In some embodiments, the device further comprises an inner surface that defines a diameter of a vertical throughhole within the device. The radius of the inner surface is half the diameter of the throughhole. In some embodiments, the radius of the inner surface is between 5 and 20 mm. In some embodiments, the device has an oval shape having a major inner radius and a minor inner radius. Preferably, the major inner radius is between 5 mm and 10 mm, and the minor inner radius is between 15 mm and 20 mm. For the purposes of the present invention, when only a single radius is recited, the major radius is contemplated.

Now referring to FIG. 13, in some embodiments of the present invention, the device of the present invention comprising two closed central recesses 131, 133.

The embodiments of the present invention wherein the device comprises a vertical throughhole are desirable because the throughhole provides a conduit for biological ingrowth from the upper vertebral endplate to the lower vertebral endplate. In some embodiments, an inter-endplate column of scar tissue is desirably formed along the height of the throughhole. This column acts as a central stop against which the inner surface of the device may abut if the device strays from the center of the endplates. Accordingly, the presence of the throughhole promotes stabilization of the device within the device space.

The throughhole also enhances the ability of the device to fold upon itself, so that it can be comfortably inserted into a minimally invasive tube or cannula and delivered to the disc space in a minimally invasive fashion.

Now referring to FIG. 14, in some embodiments of the present invention, the device has a transition zone 145 between the bearing surfaces (such as upper bearing surface 11) and the central recess (such as central throughhole 141).

In some embodiments, the device is provided with tissue ingrowth surfaces. In some embodiments, the tissue ingrowth surface is a netting attaching to the circumference of at least one of the upper, lower and inner surfaces. In some embodiments, the tissue ingrowth surface comprises a textured surface. In some embodiments, the tissue ingrowth surface comprises open porosity extending through the thickness of the device. In some embodiments, the tissue ingrowth surface comprises a resorbable material either neat or augmented with biochemical or biological agents that assist ingrowth (such as TGF-β or IGF) or reduce pain.

The difference in radii between the inner and outer surfaces define the thickness of the device. Generally, the thickness of the device depends upon the choice of the material of construction. In some embodiments using polyurethane as a material of construction, the thickness of the unloaded device is between 4 mm and 10 mm. If the thickness is less than 4 mm, the device may lack the strength need to resist axial compressive forces without collapsing. If the thickness of the device is greater than 10 mm, then excessive load may pass through the device and not be transferred into an annular hoop tension.

In some embodiments, physiologic axial compression the device of the present invention will reduce the height of the device between about 4% and 25%, preferably between 5% and 10%. By way of comparison, a natural healthy disc is believed to naturally compress between 1 mm and 5 mm in response to normal axial loads.

When the device is provided in the form of an annulus, it has two preferred annular forms. In one form, the shape is continuous, thereby forming a loop. Preferably, the loop is circular or elliptical. When the device is provided in this form, its unloaded state is typically annular, and its outer diameter is slightly greater than the annulus fibrosus to which is should conform.

Therefore, in accordance with the present invention, there is provided a prosthetic nucleus pulposus replacement device having a continuous ring shape and comprising:
a) an upper surface adapted to bear against an upper endplate,
b) a lower surface adapted to bear against a lower endplate,
c) an outer surface having a radius and adapted to conform to an inner wall of an annulus fibrosus,
d) a through hole having a radius and extending from the upper surface to the lower surface.

In the second form, the device comprises a single length having first and second ends. When these ends are brought adjacent to each other, the device forms a split-ring. When the device is provided in this form, its unloaded state is typically annular, and its outer diameter is slightly greater than the annulus fibrosus to which is should conform. In either the loop or split-ring forms, the device preferably has a circular or elliptical shape when in the disc space such that it abuts the inner wall of the annulus.

Generally, the cross-sectional shape of the device may be any shape that provides the load bearing function of the device. Now referring to FIG. 4, in some embodiments, this shape is selected from the group consisting of a circle (FIG. 4a), an oval (FIGS. 4b and 4c), a semicircle (FIG. 4d), a half-moon (FIG. 4e), a rectangle (FIGS. 4f and 4g), a square (FIG. 4h), a triangle (FIG. 4i), and an hourglass. Lastly, the cross-sectional shape may transition from one shape to another along the device's length or loop.

In some embodiments wherein the device is truly annular, the device further comprises a horizontal insertion hole extending from the outer surface to the inner surface. The hole is designed so that an insertion instrument can pass through the hole and attach to a portion of the inner surface.

Preferably, the material of construction of the device may be selected from any material that can resist compressive loads in the selected geometry and yet still deform sufficiently to transfer load to the annulus fibrosus. In some embodiments, the device is made of a material selected from the group consisting of an elastomer, a rubber, a flexible metal, a biological scaffold, a hydrogel, and a composite such that it may resist compressive loads yet still deform.

In some embodiments of the present invention, the device is deformable, preferably through its vertical cross section. When the device is deformable through its cross-section, it can be inserted through a minimal invasive surgical approach. In preferred embodiments, the deformation of the device comprises folding one half of the device upon a second half of the device by making a crease extending from the inner radius to the outer radius in diametrically opposed regions of the device. After the device is so folded, it can be easily slid into a minimally invasive tube and pushed through a small annular window in the annular ring post discectomy to enter the disc space, whereupon it expands to its second state.

The primary desirable mechanical attribute of the device is an ability to redistribute an axial compressive load. Preferably, the device does not fully accept nor fully transfer the axial compressive load. Rather, it preferably shares the axial compressive load and more preferably redistributes a portion of the axial compression loads to the annulus fibrosus as a tensile load, thereby relieving the annulus fibrosus of a relatively high compressive load after nucleotomy. The shape and materials utilized will dictate the amount of load transfer through the device and the load redistribution.

In some embodiments, the annulus will be made of a material having a compressive modulus of 2-20 MPa, preferably between 5 MPa and 7 MPa (with a more preferred value of about 6 MPa). When the compressive modulus is in this general range, the device will compress in response to a physiologic axial load, but also expand laterally against the annulus (hoop strain) and to a lesser extent inwardly. When the material has a compressive modulus greater than 7 MPa, the relatively stiff device will transfer the majority of the axial load and may buckle and press against the annulus or buckle into itself. When the material has a compressive modulus less than 5 MPa, the device will provide little to no support and the annulus fibrosus will resist the vast majority of the compressive load. Materials having a compressive modulus in the preferred range include rubber and elastomeric materials.

Therefore, in accordance with the present invention, there is provided an annular prosthetic nucleus pulposus replacement device having a modulus of compression of between 5 MPa and 7 MPa.

This modulus also can be achieved with a lower modulus material that is reinforced with mesh like polymers or metal fibers.

When the material of construction comprises a reinforcing material (such as chopped carbon fiber or an oriented continuous loop), the orientation of the reinforcement may be predetermined so as to create a non-isotropic material of construction having different compressive moduli in different directions. In some preferred embodiments having such anisotropy, the material is characterized by a higher axial compressive modulus and a relatively lower radial compressive modulus. This particular anisotropy is desirable because it allows greater redirection of the axial load to the annulus ring.

Therefore, in accordance with the present invention, there is provided an elongate prosthetic nucleus pulposus replacement device having a cross section having:
a) an axial modulus of elasticity, and
b) a radial modulus of elasticity,
wherein the axial modulus of elasticity is different than the radial modulus of elasticity.

Also in accordance with the present invention, there is provided a prosthetic nucleus pulposus replacement device comprising a polymeric matrix and reinforcement fibers.

In some embodiments, a shape memory material is incorporated into the device, preferably as the inner and/or outer surfaces of the device. Because memory metals are superelastic, they can be easily deformed and then return to their original shapes without damaging their strength or structure. Some embodiments of the present invention exploit this property of the shape memory metals to expand the height of the device once the device is inside the disc space. When the device is folded in order to insert it through a cannula the memory metal-containing outer and inner surfaces of the device are corresponding folded and the device has a lesser height. After the device has entered the disc space, the reduction of load on the device allows the memory metal-containing outer and inner surfaces of the device to expand. In some embodiments, the memory metal returns to the full height of the unloaded device. In others, the memory metal is adapted to expand to a height of the restored disc space.

The shape memory metal can be used upon only the inner surface, upon only the outer surface, or upon both surfaces. In the embodiments just discussed related to height restoration, the shape memory metals are used for both the inner and outer surfaces. In other embodiments, the device comprises a shape memory metal core surrounded by an elastomer.

Now referring to FIG. 6a, in other embodiments, the outer surface 61 of the device can comprise a shape memory metal having a predetermined vertical bow facing the outward. When this bow expands in the disc space, it pushes against the inner wall of the annulus, thereby reducing the extent of delamination space within the annulus.

In other embodiments, the inner surface of the device can comprise a shape memory metal having a predetermined vertical bow facing inward. When this bow expands in the disc space, it pushes against a nucleus augmentation material, thereby insuring the filling the remaining disc space within the nucleus augmentation material.

Now referring to FIG. 7, in other embodiments, each of the outer and inner surfaces of the device can comprise an annular shape memory metal component 71 facing outward and inward. When this loop expands in the disc space, it not only pushes against the inner wall of the annulus and nucleus augmentation material (as described above), it also pushes against the softer material of construction 73 located between the inner and outer surfaces of the device. This is desirable because it provides a restraint against elastomeric creep.

In some annular embodiments of the present invention, the device is supplemented by an injection of an in situ cured nucleus augmentation material into the center of the implanted annulus. Suitable injectable materials include polyurethanes, hydrogels and in-situ cured protein polymers. Because of the load-bearing capabilities of the annular device, the curable material is injected under virtually no load, thereby allowing the injectable augmentation material to take the shape of the throughhole and adjacent endplates. Accordingly, the cured nucleus augmentation material can have a lordotic profile corresponding to the height of the disc space. In some embodiments, a nucleus augmentation material comprising subintestinal submucosa (SIS) is added into the core as a scaffold for tissue growth.

In order to use the device of the present invention, first, a percutaneous or minimally invasive procedure is used to approach the disc. Preferably, the approach is posterolateral.

Next, a hole is cut into the disc to provide an access pathway for the device. In some embodiments, the hole is created by using a trephine or drill. The hole may be between 4 mm and 12 mm.

Next, an instrument designed to remove nucleus pulposus is inserted into the hole and into the nucleus pulposus. Preferred instruments include rongeurs and irrigated burrs. In some embodiments, the instrument include both irrigation and suction features. Once in the nucleus pulposus, the device is activated to clean out as much nucleus pulposus as possible. Since the nucleus pulposus contained many pain-causing stimulants, it is desirable to remove at least 99% of the nucleus pulposus.

Referring now to FIGS. 10-12, in some embodiments, the instrument 1 designed to remove the nucleus pulposus comprises:
a) an outer tube 3 having a proximal end opening in communication with a vacuum source (not shown), a closed distal end 10, and a lateral distal end opening 7,
b) an inner tube 9 extending from the closed distal end of the outer tube, the inner tube having a proximal end opening in communication with an irrigation source 99 and a distal end 13 having a distal end opening 15 and a rod 100 having a distal end head 17 extending from the opening,
c) a plurality of flexible protrusions 19 extending from the distal end head, wherein each flexible protrusion has a free distal end 21,
d) means for rotating the inner tube (not shown).

Because the flexible protrusions are indirectly attached to the rotating inner tube, they will likewise rotate along with the inner tube. When spun at a sufficiently high velocity, the flexible protrusions will cut the nucleus pulposus native material. Irrigation fluid provided by the inner tube will suspend the cut nucleus pulposus material therein, and the fluid containing the particles can then be vacuumed out of the body. Now referring to FIGS. 11-12, in some embodiments, the protrusions are sufficiently flexible so that they can bend in the tube's longitudinal direction. This bendability eases the insertion and removal of the instrument from the disc space.

Next, the device of the present invention is loaded onto an insertion instrument. In some embodiments, as in FIGS. 8 and 9, the device is simply a rod having a distal end adapted to hold the inner surface of the device. In some embodiments, the distal end has a shape that is complimentary to the shape of the inner surface of the device. For example, in some embodiments, the distal end has a vertical cross section having a concave shape adapted to attached to the convex inner surface of the device.

Next, the device is inserted through the hole in the annulus fibrosus and into the cavity created by the removal of the natural nucleus pulposus. If the device has been folded into an insertion cannula, it expands when unconstrained to conform to the inner wall. If the device has two ends, a first end may enter the cavity and curve along the inner wall of the annulus fibrosus in order to conform to that inner wall. In either case, the outer surface of the device conforms to at least a portion of the inner wall of the annulus fibrosus.

Lastly, insertion instrument is removed from the restored disc, and the hole in the annulus fibrosus is closed. In some embodiments, the device may sufficiently resist expulsion so as to make hole closure unnecessary.

The instrumentation provides consistent and automated disc removal though the same small annular hole (trephine hole). This invention would allow removal of the nucleus in a determined amount and shape. The extracted degenerated nucleus is then replaced with tissue friendly polymers, composites, hydrogels, bioabsorbables, or biological scaffolds that will restore disc height and maintain the motion.

We claim:

1. A method of removing a nucleus pulposus from an intervertebral disc having an annulus fibrosus, comprising the steps of:
   a) cutting a hole in the annulus fibrosus of the disc to provide an access pathway,
   b) providing an instrument comprising:
      i) an outer tube having a proximal end, a proximal end opening, a distal end and a lateral distal end opening,
      ii) an inner tube extending through the distal end of the outer tube, the inner tube having a proximal end opening in communication with an irrigation source and a distal end having a distal end opening, wherein the distal end of the outer tube contacts the inner tube,
      iii) a rod having a distal end head extending from the distal end opening of the inner tube, and
      iv) a plurality of flexible protrusions extending from the distal end head, wherein each flexible protrusion has a free distal end,
   c) inserting the distal end head through the hole and into the nucleus pulposus,
   d) rotating the distal end head so that the flexible protrusions will cut the nucleus pulposus native material, and
   e) flowing an irrigation fluid from the irrigation source into the disc to suspend the cut nucleus pulposus material therein.

2. The method of claim 1 further comprising the step of:
   f) vacuuming the fluid containing the cut particles out of the disc.

3. The method of claim 1 wherein the plurality of flexible protrusions extend only from the distal end head.

* * * * *